United States Patent [19]
deCiutiis

[11] Patent Number: 5,092,848
[45] Date of Patent: Mar. 3, 1992

[54] INTRAVENOUS CATHETER WITH BUILT-IN CUTTING TIP AND METHOD FOR MAKING THE SAME

[76] Inventor: Vincent L. deCiutiis, 254 Via Linda Vista, Redondo Beach, Calif. 90277

[21] Appl. No.: 593,574

[22] Filed: Oct. 5, 1990

Related U.S. Application Data

[63] Continuation of Ser. No. 257,456, Oct. 13, 1988, abandoned.

[51] Int. Cl.$^5$ .............................................. A61M 5/00
[52] U.S. Cl. ................................. 604/170; 604/272; 606/225
[58] Field of Search .................. 29/447; 128/334, 339; 264/230; 604/158, 164, 272–274, 170; 606/225, 167, 170

[56] References Cited

U.S. PATENT DOCUMENTS

| | | | |
|---|---|---|---|
| 2,301,495 | 11/1942 | Abegg | 29/447 |
| 2,512,569 | 6/1950 | Sattir | 604/272 |
| 3,470,604 | 10/1969 | Zenick | 604/272 X |
| 3,513,429 | 5/1970 | Helsop | 29/447 X |
| 3,584,624 | 6/1971 | deCiutiis | 604/272 X |
| 3,634,924 | 1/1972 | Blake et al. | 29/447 |
| 3,780,733 | 12/1973 | Manzor | 604/158 |
| 3,861,393 | 1/1975 | Durand | 128/347 |
| 3,918,455 | 11/1975 | Coplan | 606/225 |
| 4,169,477 | 10/1979 | Bokros | 128/334 R |
| 4,431,426 | 2/1984 | Groshong | 604/280 |
| 4,496,353 | 1/1985 | Overland et al. | 604/272 |
| 4,664,423 | 5/1987 | Rowley | 29/447 X |

Primary Examiner—John D. Yasko
Assistant Examiner—Corrine Maglione
Attorney, Agent, or Firm—Fulwider Patton Lee & Utecht

[57] ABSTRACT

An intravenous catheter includes a tubular member made from a shrinkable material that has a built-in cutting tip located at its distal end. The cutting tip is adapted to cut through tissue and create an opening in a blood vessel of a patient that is the same diameter as the outer diameter of the tubular member. The tubular member is shrinkably affixed to at least a portion of the cutting tip to prevent removal of the cutting tip during usage or insertion. Another embodiment of the intravenous catheter includes a cutting tip disposed near the distal end of a tubular member tube and having a middle portion formed from a shrinkable material surrounding both the cutting tip and tubular member. The middle portion keeps the cutting tip and tubular member together and creates an integrated unit having a smooth outer surface and a continuous outer diameter throughout.

15 Claims, 3 Drawing Sheets

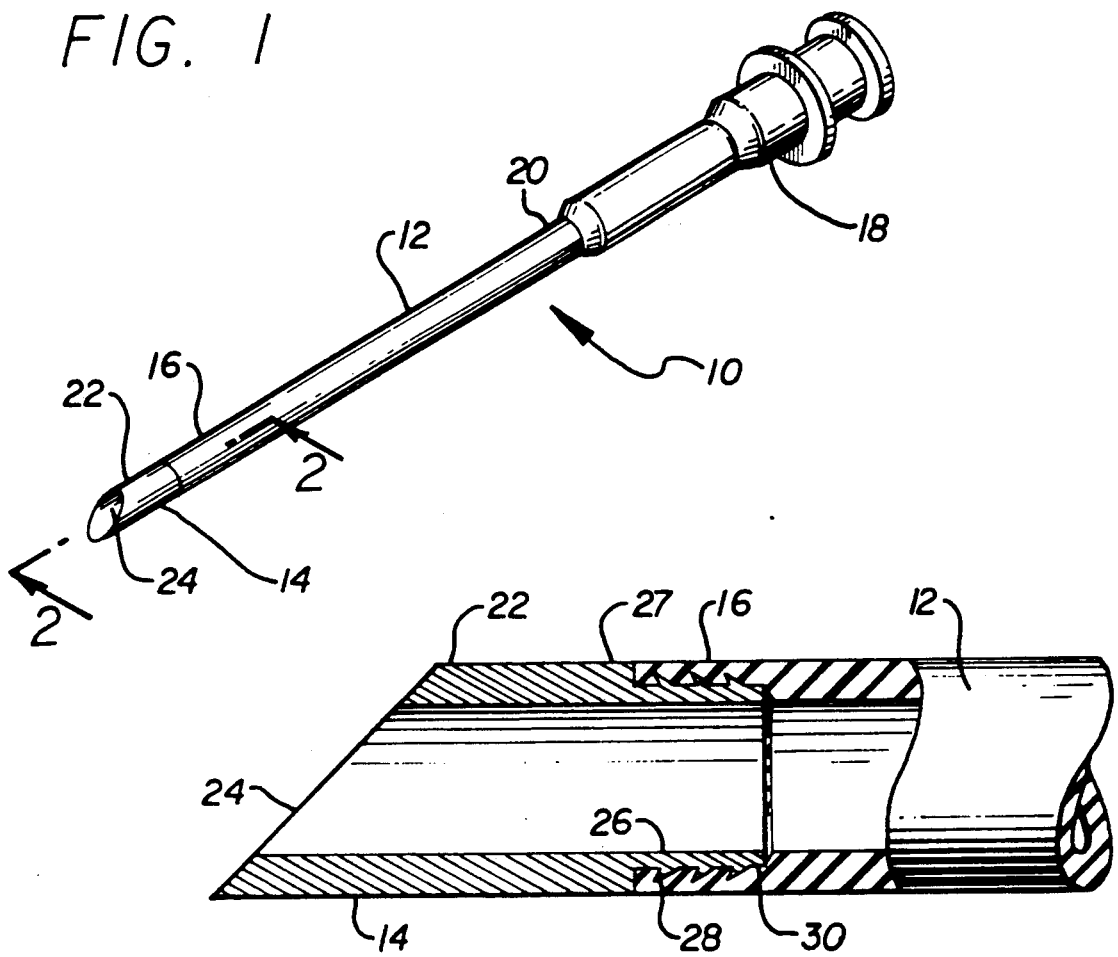
FIG. 1
FIG. 2
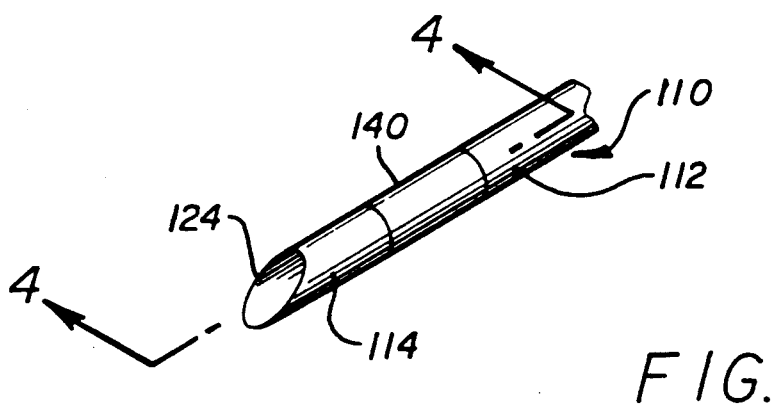
FIG. 3

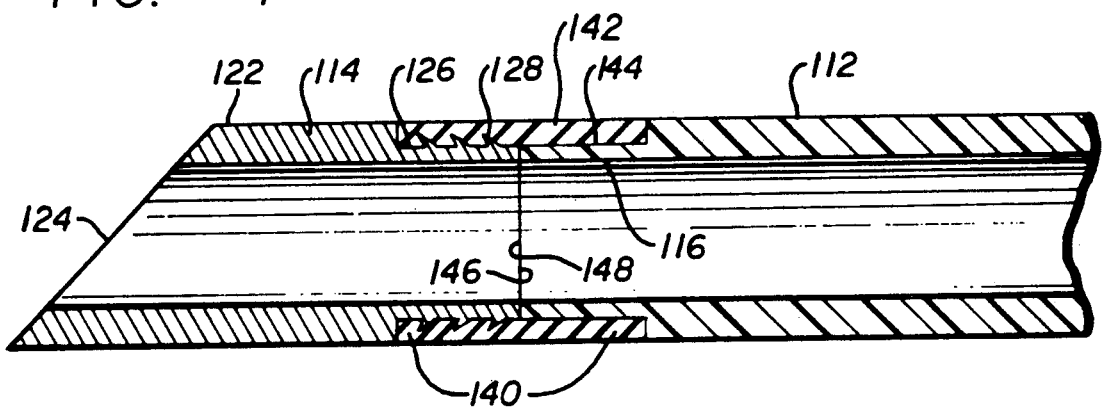
FIG. 4
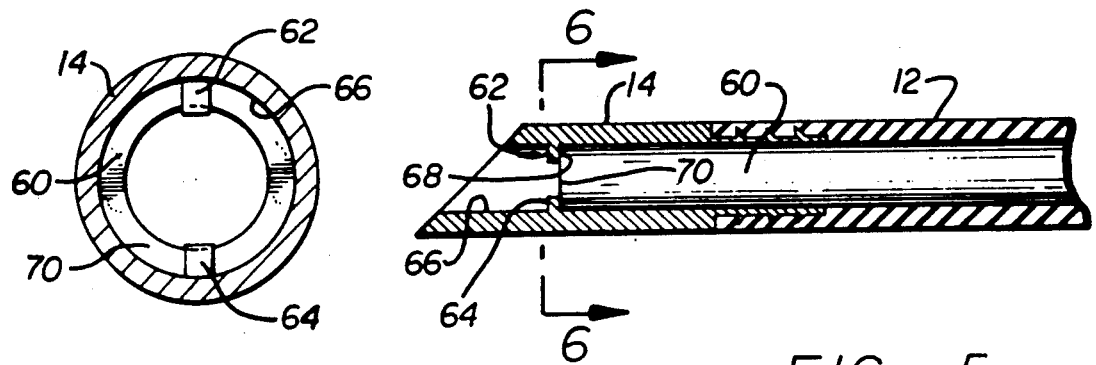
FIG. 6  FIG. 5
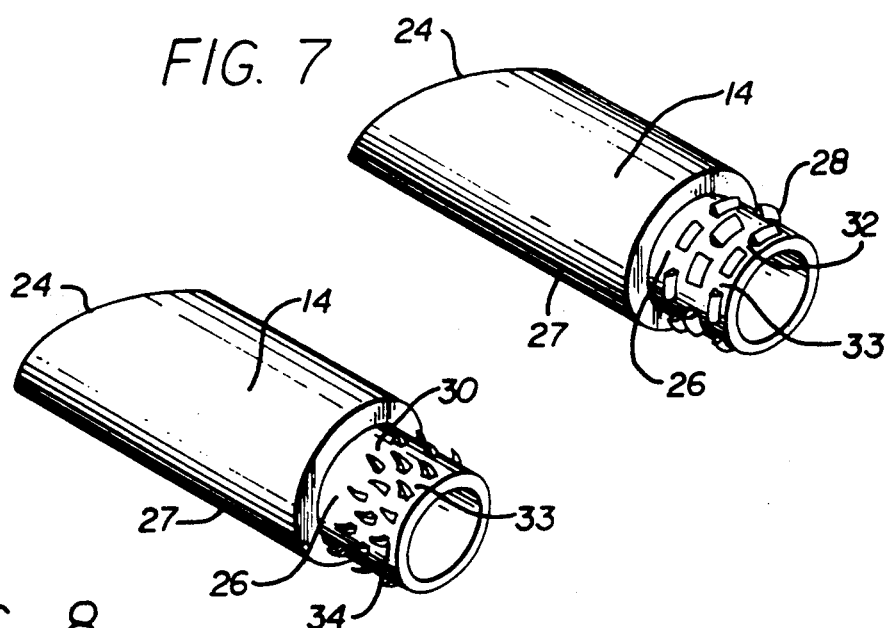
FIG. 7
FIG. 8

INTRAVENOUS CATHETER WITH BUILT-IN CUTTING TIP AND METHOD FOR MAKING THE SAME

This application is a continuation, of application Ser. No. 07/257,456, filed Oct. 13, 1988 now abandoned.

BACKGROUND OF THE INVENTION

Intravenous catheters are well-known medical devices that are used for obtaining blood samples or injecting fluids, such as blood, medication, intravenous liquids, water, and the like, into a patient's bloodstream. Throughout the years, many varieties of intravenous catheters have been developed and used, some having more success than others. Most prior art intravenous catheters require a cutting means, usually a needle, which is used to insert an elongated, hollow tube into the vein of the patient. The needle first penetrates through the skin of the patient and then pierces the vein to allow the hollow catheter tube to be inserted into the vein. After the catheter tube is inserted, the needle is removed leaving only the flexible catheter tube in place. Depending upon the desired use, the catheter tube can remain in the vein for a relatively short period of time or can remain for days or weeks at a time.

One of the more widely used intravenous catheter devices utilizes a hollow needle that has a flexible catheter tube fitted axially on the outside of the needle. The needle penetrates the skin and the wall of the vein creating a small opening for the catheter tube to pass through. However, since the outer diameter of the needle is smaller than the outer diameter of the catheter tube, the catheter tube must be forced into a smaller opening causing considerable pain and discomfort to the patient. Also, it is possible for the vein to become perforated due to the additional force needed to push the catheter tube through the smaller size opening in the vein. As a result, both the needle and the catheter tube can possibly pass entirely through the vein, rather than being inserted into the lumen of the vein. If this occurs, the vein usually becomes collapsed or ripped and cannot be used for intravenous purposes until fully healed. As a result, the catheter tube must be placed in another location in a different vein.

Another popular intravenous catheter device also utilizes a large, hollow needle which has the catheter tube placed axially within the hollow channel formed in the needle. The needle first penetrates the skin and the wall of the vein to place the catheter tube within the vein. Since the needle has a larger outer diameter than the catheter tube, an excessively larger opening is made in the wall of the vein that cannot be fully occupied by the smaller catheter tube once the needle is removed. As a result excess bleeding that can last hours and sometimes days may occur around the opening until the vein can properly heal itself around the tube to prevent further bleeding. The opening could be possibly further enlarged by the movement of the catheter tube during the changing of the dressing surrounding the catheter tube which inhibits the healing process.

A solution to the bleeding problem caused by an over-size or under-size needle is to simply utilize a needle that has the same outer diameter as the catheter tube. However, from a physical standpoint, such a catheter system could not be created using prior art needles and tubing since the insertion needle has always been removed from the vein once the catheter tube has been inserted As a result, a larger or smaller size opening would have to be formed in the patient's vein.

Therefore, there is a need for an intravenous catheter that utilizes a cutting system which creates an opening that is the same size as the outer diameter of the catheter tube. Such an intravenous catheter system would eliminate excess bleeding and should alleviate some pain since the catheter tube would not be forced into a smaller opening in the vein. To be effective, such an intravenous catheter should be easy to insert into a vein and should also be easy to manufacture.

A partial solution to this problem was developed and disclosed in my U.S. Pat. No. 3,584,624 issued June 15, 1971 and now expired. This invention utilized a flexible tubular portion that was affixed to a cutting tip by permanent adhesive. While the structure was effective, one of the major problems encountered in manufacturing this device was the enormous amount of time and effort that was needed to properly glue or adhesively affix the cutting tip to the catheter tube. This problem prevented the device from being mass produced since the bonding of the cutting tip to the tubing is so critical. The cutting tip cannot become unattached from the tubing while in the vein since the tip would enter the bloodstream and cause imminent death to the patient. Therefore, there is a need for an improved structure and method for permanently affixing the cutting tip to the catheter tube which does not require great effort yet achieves a solid and dependable bond.

SUMMARY OF THE INVENTION

The purpose of the present invention is to provide an intravenous catheter with a built-in cutting tip which is designed to remain permanently with the catheter tube once inserted into the vein of a patient. The present invention provides an advantageous design and method over my previous catheter device since less effort is required to permanently affix the cutting tip to the catheter tube resulting in a unit that is more dependable and can be more easily mass produced.

The present invention utilizes a flexible catheter tube or tubular member that is made from a material which can be shrinkably affixed to a portion of a cutting tip to form an integral unit. A portion of the catheter tube is placed over a specially designed portion of the cutting tip to allow the tube to be shrinkably affixed to the tip upon the application of an external shrinking source. This external shrinking source can be one of many sources that will allow at least part of the tubing material to be shrunk onto the cutting tip. The selection of tubing material will depend upon which external shrinking source is used.

The cutting tip includes holding means that can take the form of outwardly extending, angular serrations that point outward towards the distal end of the cutting tip. This particular orientation helps maintain the catheter tube on the cutting tip after the tube is shrunk in place. These angular serrations also form cavities which receive the tube material that flows once the catheter tube is shrunk onto the cutting tip. This particular structure enhances the ability of the cutting tip to remain affixed to the catheter tube.

An alternative embodiment of the intravenous catheter includes a similar cutting tip, conventional catheter tubing, and a layer of shrinkable material that surrounds portions of both the cutting tip and the catheter tubing to hold the elements together. This shrinkable material is placed on the outer surface of the cutting tip and catheter tube and is shrinkably affixed to these elements after being subjected to the external shrinking source. The layer of material, usually a thermoplastic material, forms an extremely tight bond with the surface of cutting tip and catheter tubing resulting in the cutting tip being permanently affixed to the catheter tubing.

Another embodiment includes the placement of a catheter tube over the holding portion of a cutting tip. A similar layer of shrinkable material can be placed and shrunk over the outer surface of the tube. This layer of shrinkable material acts somewhat like a "clamp" to maintain the catheter tube on the cutting tip.

These other embodiments of the present invention can also include holding means located on the cutting tip in the form of angular serrations which also help promote affixation of the shrinkable material or catheter tube to the cutting tip. In each embodiment of the present invention, a stylet, usually a needle such as a spinal needle, can be inserted into the proximal end of the catheter tube and into the cutting tip to temporarily stiffen the flexible catheter tube. This stylet merely provides rigidity to the flexible catheter tube during insertion and can be easily removed once the catheter tube is in place in the vein of the patient.

Other features and advantages of the present invention will become apparent from the following detailed description, taken in conjunction with the accompanying drawings, which illustrate by way of example, the principles of the invention.

BRIEF DESCRIPTION OF THE DRAWINGS

FIG. 1 is a perspective view of the intravenous catheter with a built-in cutting tip made in accordance with the present invention.

FIG. 2 is a cross-sectional, side elevational view of the structure taken along line 2—2 of FIG. 1.

FIG. 3 is a partial perspective view showing another embodiment of an intravenous catheter with a built-in cutting tip built in accordance with the present invention.

FIG. 4 is a cross-sectional side view of the structure taken along line 4—4 of FIG. 3.

FIG. 5 is a cross-sectional side view showing the improved cutting tip and a stylet as the stylet strikes abutting means located within the cutting tip.

FIG. 6 is a partial cross-sectional view showing the stylet within the catheter tube taken along line 6—6 of FIG. 5.

FIG. 7 is a perspective view of one embodiment of an improved cutting tip made in accordance with the present invention.

FIG. 8 is a perspective view showing another embodiment of an improved cutting tip made in accordance with the present invention.

DETAILED DESCRIPTION OF THE PREFERRED EMBODIMENTS

Figure 9:
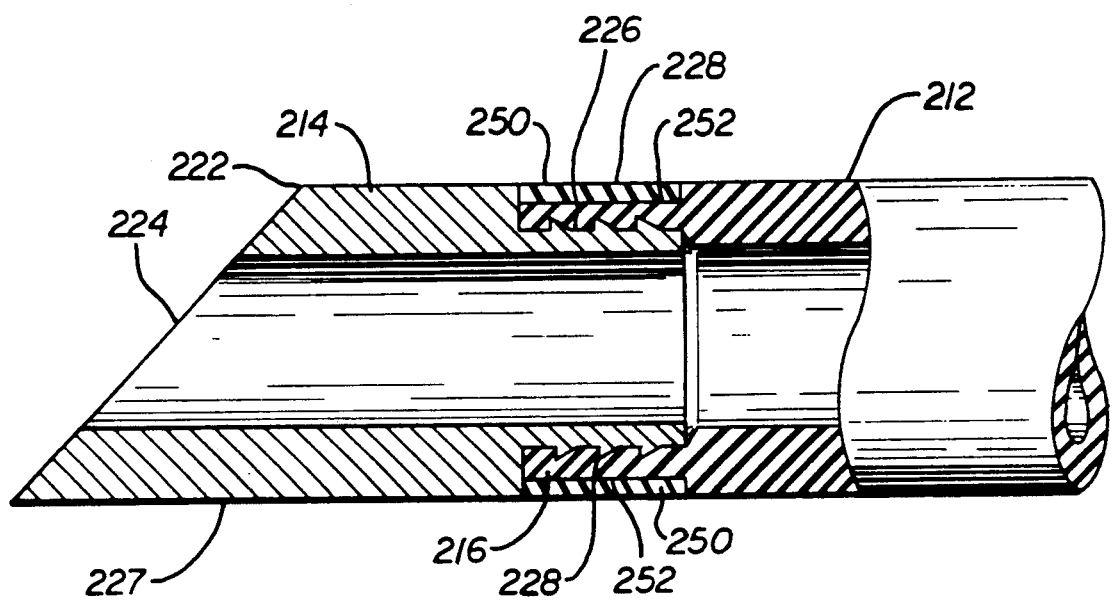
FIG. 9 is a cross-sectional view of another embodiment of an intravenous catheter with a built-in cutting tip made in accordance with the present invention.

The present invention provides an intravenous catheter with a built-in cutting tip which has a continuous external diameter from cutting tip to the proximal end of the catheter tubing. The cutting tip produces an opening in a blood vessel of a patient which is the same size as the outer diameter of the catheter tubing, thus, self-sealing the blood vessel with respect to the catheter tube to minimize blood leakage.

With reference to FIG. 1, an improved intravenous catheter system 10 includes an elongated, flexible catheter tube or tubular member 12 having cutting means in the form of a cutting tip 14 located at the distal end 16 of the member 12. A conventional medical connector 18 is permanently attached to a proximal end 20 of the tubular member 12 and functions as an independent source for introducing medication, blood, transfusion liquids, and the like, into the intravenous tubular, once it is placed in the blood vessel of a patient. It should be appreciated that the connector 18 can be any one of a number of commercially available connectors such as a "L" or "T" connector or other connectors which are readily available depending upon the particular use of the catheter system.

Referring now to FIG. 2, a cross-sectional view of the cutting tip 14 and tubular member 12 is shown in greater detail to show the interconnection between these two elements The cutting tip 14 has a general cylindrical shape and includes a distal end 22 which includes a cutting edge 24 to be used in penetrating the skin and wall of the blood vessel of the patient during insertion. The cutting tip 14 also includes a proximal end portion 26 which receives the distal end 16 of the tubular member 12. As is seen in FIG. 2, the distal end 22 of the cutting tip 14 has the same outer diameter as the tubular member 12 in order to create a continuous, smooth outer surface 27. In order to achieve this structure, the proximal end portion 26 of the cutting tip must be somewhat recessed from the rest of the outer surface of the cutting tip to allow at least a portion of the tubular member 12 to fit over that portion. The tubular member 12 must be made from a material which is capable of shrinkage when subjected to an external shrinkage source to allow the tubular member 12 to be shrinkably affixed to the cutting tip.

The proximal end portion 26 includes holding means usually in the form of angular serrations 28 (see FIG. 7) which extend from the outer surface 30 and extend outward towards the distal end 22 of the cutting tip. These angular serrations 28 are generally rows of outwardly projecting ridges that can be arranged in parallel rows with occasional intermediate spaces 32 (shown in FIG. 7) that help hold the tubular member to the cutting tip and prevent the cutting tip from turning with the tubular member. Spaces 33 between the rows of angular serrations allow the tubing material to flow into them during the shrinking process. Once the tubing material cools down, the material is formed around the ridges and remains within the spaces 33 to help hold the tubular member to the cutting tip.

Another form of holding means located on the cutting tip are shown in FIG. 8 as upwardly extending fingers 34 which provide additional surface area that can be encapsulated by the flowing tubing during the shrinking procedure. These upwardly extending fingers 34 can also be oriented towards the distal end of the cutting tip to help prevent the tubular member from becoming separated from the cutting tip when the catheter unit is being inserted into the patient or when the catheter tubing remains in the blood vessel of the patient.

FIGS. 3 and 4 show another embodiment of the present invention used to maintain the cutting tip 114 and tubular member 12 together to form an integral structure. This embodiment includes many similar elements found in the embodiment shown in FIGS. 1 and 2. Like elements in FIGS. 3 and 4 will be designated by the addition of a prefix "1" for clarity. FIG. 3 shows a middle portion 140 formed around the cutting tip 114 and tubular member 112. This middle portion 140 is made from a layer of shrinkable material 142 such as thermoplastic or similar material which is shrinkable by thermal, irradiation, or other shrinking methods. The middle portion 140 provides an advantageous means for maintaining the cutting tip together with the tubular member.

Referring now specifically to FIG. 4, the cutting tip 114 used in this embodiment can be similar to the cutting tips shown in FIGS. 2, 7, and 8, except that the proximal end portion 126 formed on this cutting tip does not usually need as deep a recess as the cutting tips shown in these other figures. This is due to the fact that the middle portion 140 is formed with a very thin layer of shrinkable material 142 which provides a sufficient connection to maintain the cutting tip with the tubular member. As is shown in FIG. 4, the distal end 116 of the tubular member 112 may also have a slight formed recessed portion 144 for receiving the layer of shrinkable material 142. However, this recessed portion 144 may not be necessary if the layer of shrinkable material is thin and does not inverse the outer diameter of the tubular member. The cutting tip 114 can also include holding means such as the angular serrations or upwardly extending fingers similar to those shown in FIGS. 7 and 8.

The intravenous catheter shown in FIGS. 3 and 4 is formed by first aligning and abutting the proximal edge 146 of the cutting tip 114 with the distal edge 148 of the tubular member 112. Once these two members are properly aligned with one another, a single layer or several layers of the shrinkable material can be placed around the recessed portions of the cutting tip and tubular member to form the middle portion 140. They layer or layers of shrinkable material at first may be placed slightly above the outer surfaces of the cutting tip and tubular member to allow the material to shrink flush with these surfaces after being subjected to the external shrinking source. After the material is in place, it can then be subjected to an appropriate amount of hat, irradiation or other source necessary to shrink the material over the outer surfaces of the cutting tip and tubular member to provide an extremely strong bond. The result is a single continuous outer surface extending from the cutting tip to the proximal end of the tubular member.

It should be appreciated that the tubular member used in the embodiment shown in FIGS. 3 and 4 has to be somewhat stiffer than the tubing used in the other embodiment of the invention. This additional rigidity is needed to enable the tubular member to remain properly affixed to the layer of shrinkable material. If the tubing is too soft, it is possible for the tubing to collapse and become loosened from the material. To alleviate this problem it is possible to utilize tubing that has more rigidity to retain the layer of shrinkable material.

During the manufacture of the catheter unit shown in FIGS. 3 and 4, a stylet or mandrel could first be inserted into the tubular member to provide additional rigidity. After the cutting tip is aligned with the tubular member, the layer of shrinkable material can be placed and shrunk over the recessed end of the tubular member. During the shrinking process, an adhesive-type bond may form between the outer surface of the tubular member and the shrinkable material due to the source that shrinks or "melts" the material in place. Preferably, the materials making up the tubular member and shrinkable layer of the embodiment should be chosen to create this additional intermeshing of materials since an even stronger bond will be achieved.

An additional embodiment of the present invention is also shown in FIG. 9. Again, this figure includes using similar elements as found in FIGS. 1 and 2. Like elements will be designated by similar reference characters with a prefix "2" in FIG. 9. This figure shows a cutting tip 214 having a similar proximal end portion 226 as shown in the other embodiments. In this embodiment, the tubular member 212 is placed over the proximal end portion 226 as was done in the embodiment shown in FIGS. 1 and 2. However, a layer of shrinkable material 250 is place over the outer surface of the tubular member to create a shrinkable bank which helps maintain the tubular member on the cutting tip. This layer of shrinkable material 250 acts somewhat like a "clamp" to help maintain the two elements together. Again, the tubular member 212 may have a recess 252 for receiving the layer of shrinkable material. This recess 252 may be actually preformed into the tubular member if needed. Again, the shrinkable material is designed to be shrunk flush with the outer surfaces of the cutting tip and flexible tubular member to create a continuous outer surface. It is possible for the shrinkable material to compress the tubular member 212 once it is shrunk in place. If the layer of shrinkable material is sufficiently thin, than the formed recess on the outer surface of the tubular member may not be necessary. This embodiment also includes holding means in the form of angular serrations 228 which are similar to those shown in FIGS. 7 and 8.

The present invention also utilizes force transmitting means in the form of an internal stylet which can be placed within the tubular and cutting tip to provide rigidity to the structure when it is being inserted into the patient. This same stylet can be used with each embodiment of the present invention. Turning now to FIGS. 5 and 6, the stylet 60 is usually a hollow tube or needle which is slidable within the tubular member 12 and cutting tip 14. Usually, a spinal needle can be used and inserted in the tubular member 12 and cutting tip 14 to provide added rigidity to the structure.

The cutting tip 14 may further include abutting means shown in FIGS. 5 and 6 as a pair of upper and lower abutments 62 and 64 are located within the internal opening 66 formed in the cutting tip. These abutments are integral with the cutting tip and provide a bearing surface 68 for the tip 70 of the stylet 60 to contact during insertion. Preferably, the abutments are small projecting extensions that do not interfere with the size of the inner diameter of the cutting tip. If the abutment is too large or is a continuous projection formed in the cutting tip, then it is possible that the flow rate of the fluid through the tip could change. For this reason, the abutments should not be too pronounced to prevent possible adverse flow changes past the cutting tip.

The stylet 60 is capable of transmitting a force to the cutting tip 14 that allows the cutting edge of the tip to penetrate through the skin and through the wall of the blood vessel. Once the cutting tip 14 has penetrated into the blood vessel and the tubular member has been properly placed within the blood vessel, then the stylet can be removed through the opening in the proximal end of the catheter tube. The tubular member will remain flexible to prevent any discomfort while remaining in the patient.

It is preferable to place the abutting means within the cutting tip rather than at the proximal edge of the tip since a sizeable amount of force is usually required to enable the cutting tip to penetrate both through the skin and wall of the blood vessel of the patient. If the force is directed right behind the cutting tip, it is possible for the tip of the stylet to misdirect the transmitted force at an angle offset from the centerline of the cutting tip, which can cause a wobbly cutting action (called "coring") to occur. This cutting action is undesirable since it creates a larger opening both in the skin and blood vessel which defeats the self-sealing feature of the present invention.

The cutting tip may be made from metal such as stainless steel or from a hard cutting plastic material such as methyl methacrylate which is a known and widely used material in the medical profession. The cutting tip can be machined or created by using injection molding techniques. The manner in which the cutting tip is made does not depart from the spirit and scope of the invention.

The shrinking method used in accordance with the present invention can be any one of a number of shrinking techniques well-known in the art. For example, thermal sealing or bonding can be used in which direct application of heat is used to join the cutting tip with the tubular member. For example, in the embodiment shown in FIGS. 1 and 2, the tubular member would have to be made from a material which would at least partially shrink once subjected to the application of direct heat. Also, pressure is sometimes simultaneously added to aid in the thermal bonding. The material would have to be shrinkable but yet retain its strength in order to prevent possible breakage at the point of attachment to the cutting tip. The tubular member could be made from a teflon-type material which is manufactured and sold by the Dupont Company of the United States. Any other similar material which achieves the desired results could also be used.

Another external shrinking source used to shrink the tubular member onto the cutting tip could utilize irradiation shrinking techniques. In this type of shrinkage, the tubular member is made from a material that shrinks when exposed to some form of irradiation, usually ultraviolet rays or lights. The irradiation may cause the material to melt which again causes shrinkage to occur which can create a tight bond needed between the tubular member and the cutting tip. Such irradiation techniques are already commercially used in other shrinking, applications, for example, for shrinking thermal plastic over objects for storage. The tubular member can again be made from a teflon-type material that is manufactured and sold by the Dupont Company of the United States.

The embodiments shown in FIGS. 3, 4, and 9 can use a similar material or hard plastic cutting tip with a flexible tubular member made from a material such as nylon or teflon that is commercially available and manufactured by a number of companies worldwide. The layer of shrinkable material used with these embodiments can be made from a thermo plastic material such as Silastic which is also manufactured by the Dupont Company of the United States. However, any material which can be shrunk by any external source can be used in these embodiments.

Preferably, the materials used to form the cutting tip, tubular member, and layer of shrinkable material should be of a type that is medically approved by the United States Food and Drug Administration. The use of pre-approved materials will prevent the possibility of possible delays due to obtaining approval before the unit can be sold or used in the United States.

The embodiment of the intravenous catheter shown in FIGS. 1 and 2 can be made by first placing at least a portion of the tubular member over the proximal end portion of the cutting tip. This step may result in the tubing bulging somewhat outward due to the angular serrations or upraised fingers located on the proximal end portion. However, this bulge will dissipate once the material is subjected to the external shrinking source.

The next step is to subject at least this overlapping portion of the tubing and cutting tip to the respective shrinking source, depending upon the material characteristics of the tubing material. Once the material starts to shrink, it will "flow" between the spaces located between the angular serrations on the cutting tip, thus reducing the bulge that first results when the tube is placed on the cutting tip. The result is an intravenous catheter which incorporates a flexible tubular member with a built-in cutting tip that are shrinkably affixed together to form an integral unit having a continuous outer diameter.

From the above it may be seen that the present invention represents a simple and elegant solution to the problems associated in prior art intravenous catheters. The built-in cutting tip is permanently affixed to the tubular member and remains within the patient during usage, thereby eliminating the need to create a larger or smaller opening in the vein for the catheter tube to fit through. As a result, there is a minimal loss of blood and similar loss of discomfort to the patient when the present invention is placed in the blood vessel of a patient.

While particular forms of the invention have been illustrated and described, it will be apparent to those skilled in the art that various modifications can be made without departing from the spirit and scope of the invention. Accordingly, it is not intended that the invention be limited except by the appended claims.

What is claimed is:

1. An intravenous catheter comprising:
   a tubular member having a constant outer diameter and a distal end;
   a cutting tip having a constant outer diameter which is the same as the outer diameter of said tubular member and including a distal cutting end and a recessed proximal end portion adapted to receive said distal end of said tubular member, said tubular member being placed on said proximal end portion; and
   a layer of shrinkable thermoplastic material surrounding the outer surface of the tubular member near said distal end to maintain said tubular member on said proximal end portion, said layer of shrinkable material being shrunk flush with the other surfaces of said cutting tip and said tubular member.

2. The intravenous catheter as defined in claim 1 wherein said tubular member includes a recessed portion formed near its distal end for receiving said layer of shrinkable material.

3. The intravenous catheter as defined in claim 1 wherein said proximal end portion further includes holding means defined therein for holding said tubular member.

4. The intravenous catheter as defined in claim 3 wherein said holding means comprise at least one angular serration extending from the recessed proximal end portion of said cutting tip, each angular serration having at least three side surfaces.

5. The intravenous catheter as defined in claim 3 wherein said holding means comprise a multiplicity of upwardly projecting finger members each spaced apart from one another and terminating at a point to protrude into said tubular member.

6. An intravenous catheter comprising:
   a tubular member having an constant outer diameter and a distal end;
   a cutting tip having an outer diameter that is the same as the outer diameter of said tubular member and including a distal cutting end and a recessed proximal end portion including a proximal edge, said proximal edge being in substantially abutting relationship with said distal end of said tubular member, said cutting tip having an opening extending from said distal cutting end to said proximal edge; and
   at least one layer of shrinkable theremoplastic material surrounding said recessed end portion and said distal end of said tubular member, said layer being shrinkably affixed to said cutting tip and said tubular member, said layer of shrinkable material being shrunk flush with the outer surfaces of said cutting tip and said tubular member.

7. The intravenous catheter as defined in claim 6 wherein said proximal end portion further includes holding means defined therein for holding said layer of shrinkable material.

8. The intravenous catheter as defined in claim 7 wherein said holding means comprise at least one angular serration extending from the outer surface of said proximal end portion adapted to form a structure that helps receive and hold said layer of shrinkable material.

9. The intravenous catheter as defined in claim 7 wherein said holding means comprise a multiplicity of upwardly projecting finger members each spaced apart from one another, each finger member terminating at a point to protrude into said tubular member to hold it to said cutting tip.

10. The intravenous catheter as defined in claim 6 wherein said tubular member includes a recessed portion formed near its distal end for receiving said layer of shrinkable material.

11. An intravenous catheter comprising:
    a tubular member made from a shrinkable thermoplastic material having a distal end and an outer surface;
    a cutting tip having a distal cutting end and a recessed proximal end portion adapted to receive said distal end of said tubular member, said cutting tip having a longitudinal opening extending from said distal cutting end to said proximal end portion and having an outer surface that is continuous with said outer surface of said tubular member, said tubular member being shrinkably affixed to said proximal end portion; and
    a multiplicity of upwardly projecting finger members adapted to extend upward from the recessed proximal end portion of the cutting tip, each finger member being spaced from one another and terminating at a tip to protrude into said tubular member.

12. A method for making an intravenous catheter from a tubular member having a constant outer diameter and a cutting tip having a distal cutting edge and a recessed proximal end portion, the cutting tip having a constant outer diameter which is the same as the tubular member, comprising the steps of:
    placing the distal end of the tubular member in close proximity to the proximal end of the cutting tip;
    placing at least one layer of a shrinkable thermoplastic material around at least a portion of cutting tip and a portion of the tubular member; and
    subjecting the shrinkable material to an external source that shrinks the shrinkable material flush with the outer surfaces of the cutting tip and tubular member.

13. An intravenous catheter manufactured in accordance with the method of claim 12.

14. A method for making an intravenous catheter from a tubular member having constant outer diameter and a distal end and a cutting tip having a distal cutting edge and a recessed proximal end portion, said cutting tip having a constant outer diameter which is the same as the tubular member, comprising the steps of:
    placing the distal end of the tubular member over the proximal end portion of the cutting tip;
    placing shrinkable thermoplastic material around the outer surface of the tubular member near its distal end; and
    subjecting the shrinkable material to an external shrinking source which shrinks the material flush with the outer surfaces of the cutting tip and tubular member.

15. An intravenous catheter manufactured in accordance with the method of claim 14.

* * * * *